United States Patent [19]

Takamizawa et al.

[11] Patent Number: 5,693,497
[45] Date of Patent: Dec. 2, 1997

[54] **PROCESS FOR EXPRESSING THE HEPATITIS B VIRUS ANTIGEN USING A *SACCHAROMYCES CEREVISIAE* TRANSFORMANT**

[75] Inventors: Akihisa Takamizawa, Kanonzi; Hiroyuki Fujita; Sadao Manabe, both of Mitoyo-gun; Masahiko Kato, Kanonzi; Juichiro Osame, Mitoyo-gun; Iwao Yoshida; Takeo Konobe, both of Kanonzi; Keisuke Takaku, Suita, all of Japan

[73] Assignee: The Research Foundation for Microbial Diseases of Osaka University, Suita, Japan

[21] Appl. No.: 378,011

[22] Filed: Jan. 25, 1995

Related U.S. Application Data

[62] Division of Ser. No. 902,494, Jun. 23, 1992, abandoned, which is a continuation of Ser. No. 61,518, Jun. 15, 1987, abandoned.

[30] Foreign Application Priority Data

Jun. 18, 1986 [JP] Japan ................................ 61-143412

[51] Int. Cl.$^6$ ................ C12P 21/02; C12N 1/19; C12N 15/51
[52] U.S. Cl. .................... 435/69.3; 435/254.21; 435/320.1; 435/942; 424/189.1; 536/23.72
[58] Field of Search ................ 435/69.3, 254.21, 435/942, 320.1; 424/189.1; 536/23.72

[56] References Cited

U.S. PATENT DOCUMENTS 4,722,840  2/1988  Valenzuela et al. .
4,935,235  6/1990  Rutter et al. .

*Primary Examiner*—Anthony C. Caputa
*Attorney, Agent, or Firm*—Armstrong, Westerman, Hattori, McLeland & Naughton

[57] ABSTRACT

There is disclosed an antigen comprising an amino acid sequence of the surface antigen of a hepatitis B virus. The present antigen can be produced easily and safely at low cost by means of recombinant DNA technique. The present antigen can be used as an effective vaccine and diagnostic for hepatitis B.

1 Claim, 8 Drawing Sheets

FIG. 3a

```
pBHI03-ME5 : ------  ATACCCATTTGGGATAAGGTAAACATCTTTGAATTGTCGAAATGAAACGTATATAAG
pBHI03-CT  : ------  ATACCCATTTGGGATAAGGTAAACATCTTTGAATTGTCGAAATGAAACGTATATAAG
                                                                         -87
                                                                         -89
                                                                         Hogness box CGCTGATGTTTTGCTAAGTCGAGGTTAGTATGGCTTCATCTCTCATGAGAATAAGAACAACAAATAGAGCTAGCCG
CGCTGATGTTTTGCTAAGTCGAGGTTAGTATGGCTTCATCTCTCATGAGAATAAGAAC-----------------

1                                      30                                      60
    ATG TCG AGG ACT GGG GAC CCT GCA CCG AAC ATG GAG AAC ACA ACA TCA GGA TTC CTA GGA
    Met Ser Arg Thr Gly Asp Pro Ala Pro Asn Met Glu Asn Thr Thr Ser Gly Phe Leu Gly
    --- --- --- -GG ACT GGG GAC CCT GCA CCG AAC ATG GAG AAC ACA ACA TCA GGA TTC CTA GGA
                    Met Glu Asn Thr Thr Ser Gly Phe Leu Gly
                    1                                      30
```

FIG. 3b

```
CCC CTG CTC GTG TTA CAG GCG GGG TTT TTG ACA AGA ATC CTC ACA ATA CCA CAG
Pro Leu Leu Val Leu Gln Ala Gly Phe Leu Thr Arg Ile Leu Thr Ile Pro Gln
                                90                                   120
CCC CTG CTC GTG TTA CAG GCG GGG TTT TTG ACA AGA ATC CTC ACA ATA CCA CAG
Pro Leu Leu Val Leu Gln Ala Gly Phe Leu Thr Arg Ile Leu Thr Ile Pro Gln
                                60                                    90

AGT CTA GAC TCG TGG ACT TCT CTC AAT TTT CTA GGG GGA CCC ACG TGT CCT GGC
Ser Leu Asp Ser Trp Thr Ser Leu Asn Phe Leu Gly Gly Ala Pro Thr Cys Pro Gly
                                150                                  180
AGT CTA GAC TCG TGG ACT TCT CTC AAT TTT CTA GGG GGA CCC ACG TGT CCT GGC
Ser Leu Asp Ser Trp Thr Ser Leu Asn Phe Leu Gly Gly Ala Pro Thr Cys Pro Gly
                                120                                  150

CAA AAT TCG CAG TCC CCA ACC TCC AAT CAC TCA ACC TCT CCT CCA ATT TGT CCT
Gln Asn Ser Gln Ser Pro Thr Ser Asn His Ser Thr Ser Pro Pro Ile Cys Pro
                                210                                  240
CAA AAT TCG CAG TCC CCA ACC TCC AAT CAC TCA ACC TCT CCT CCA ATT TGT CCT
Gln Asn Ser Gln Ser Pro Thr Ser Asn His Ser Thr Ser Pro Pro Ile Cys Pro
                                180                                  210
```

FIG. 3c

```
                                                       270                                    300
GGC TAT CGC TGG ATG TGT CTG CGG CGT TTT ATA TTC CTC TTC ATC CTG CTG CTA TGC
Gly Tyr Arg Trp Met Cys Leu Arg Arg Phe Ile Phe Leu Phe Ile Leu Leu Leu Cys
Gly Tyr Arg Trp Met Cys Leu Arg Arg Phe Ile Phe Leu Phe Ile Leu Leu Leu Cys
                                                       240                                    270
                                                       330                                    360
CTC ATC TTC TTG TTG GTT CTT CTG GAC TAC CAA GGT ATG TTG CCC GTT TGT CCT CTA CTT
Leu Ile Phe Leu Leu Val Leu Leu Asp Tyr Gln Gly Met Leu Pro Val Cys Pro Leu Leu
Leu Ile Phe Leu Leu Val Leu Leu Asp Tyr Gln Gly Met Leu Pro Val Cys Pro Leu Leu
                                                       300                                    330
                                                       390                                    420
CCA GGA ACA TCA ACT ACC AGC ACG GGA CCA TGC AAG ACC TGC ACG ATT CCT GCT CAA GGA
Pro Gly Thr Ser Thr Thr Ser Thr Gly Pro Cys Lys Thr Cys Thr Ile Pro Ala Gln Gly
Pro Gly Thr Ser Thr Thr Ser Thr Gly Pro Cys Lys Thr Cys Thr Ile Pro Ala Gln Gly
                                                       360                                    390
```

FIG. 3d

```
ACC TCT ATG TTT CCC TCT TGT TGC TGT     AAA CCT TCG GAC GGA AAC TGC ACT TGT ATT
Thr Ser Met Phe Pro Ser Cys Cys Cys     Lys Pro Ser Asp Gly Asn Cys Thr Cys Ile
                                450                                         480
ACC TCT ATG TTT CCC TCT TGT TGC TGT     AAA CCT TCG GAC GGA AAC TGC ACT TGT ATT
Thr Ser Met Phe Pro Ser Cys Cys Cys     Lys Pro Ser Asp Gly Asn Cys Thr Cys Ile
                                420                                         450

CCC ATC CCA TCA TCC TGG GCT TTC GCA     AGA TTC CTA TGG GAG TGG GCC TCA GTC CGT
Pro Ile Pro Ser Ser Trp Ala Phe Ala     Arg Phe Leu Trp Glu Trp Ala Ser Val Arg
                                510                                         540
CCC ATC CCA TCA TCC TGG GCT TTC GCA     AGA TTC CTA TGG GAG TGG GCC TCA GTC CGT
Pro Ile Pro Ser Ser Trp Ala Phe Ala     Arg Phe Leu Trp Glu Trp Ala Ser Val Arg
                                480                                         510

TCC TGG CTC AGT TTA CTA GTG CCA TTT     CAG TGG TTC GTA GGG CTT TCC CCC ACT GTT
Ser Trp Leu Ser Leu Leu Val Pro Phe     Gln Trp Phe Val Gly Leu Ser Pro Thr Val
                                570                                         600
TCC TGG CTC AGT TTA CTA GTG CCA TTT     CAG TGG TTC GTA GGG CTT TCC CCC ACT GTT
Ser Trp Leu Ser Leu Leu Val Pro Phe     Gln Trp Phe Val Gly Leu Ser Pro Thr Val
                                540                                         570
```

FIG. 3e

```
TGG CTT TCA GTT ATA TGG ATG ATG TGG GGG CCA AGT CTG TAC AAC ATC TTG AGT
Trp Leu Ser Val Ile Trp Met Met Trp Gly Pro Ser Leu Tyr Asn Ile Leu Ser
                          630                                       660
TGG CTT TCA GTT ATA TGG ATG ATG TGG GGG CCA AGT CTG TAC AAC ATC TTG AGT
Trp Leu Ser Val Ile Trp Met Met Trp Gly Pro Ser Leu Tyr Asn Ile Leu Ser
                          600                                       630

CCC TTT TTA CCG CTA TTA CCA ATT TTC TGT CTT TGG GTA TAC ATT :708 nucleotides
Pro Phe Leu Pro Leu Leu Pro Ile Phe Cys Leu Trp Val Tyr Ile :236 amino acids
                                  690
CCC TTT TTA CCG CTA TTA CCA ATT TTC TGT CTT TGG GTA TAC ATT :678 nucleotides
Pro Phe Leu Pro Leu Leu Pro Ile Phe Cys Leu Trp Val Tyr Ile :226 amino acids
                                  660
```

PROCESS FOR EXPRESSING THE HEPATITIS B VIRUS ANTIGEN USING A *SACCHAROMYCES CEREVISIAE* TRANSFORMANT

This is a division of application Ser. No. 07/902,494, filed Jun. 23, 1992, now abandoned which was a continuation of parent application Ser. No. 07/061,518, filed Jun. 15, 1987, now abandoned.

The present invention relates to a hepatitis B virus antigen (hereinafter often referred to as "HBV antigen") containing hepatitis B virus surface antigen (hereinafter often referred to as "HBs antigen"). More particularly, the present invention is concerned with an HBV antigen comprising an HBs antigen and, linked thereto at its N-terminus, a peptide of 10 amino acids. The peptide of 10 amino acids consists of a methionine residue and a sequence of 9 amino acids which is part of the pre-HBs antigen (hereinafter often referred to as "PreS") which is a polypeptide occasionally linked to the N-terminus of the HBs antigen in a natural state. The antigen according to the present invention has a high purity and is uniform in quality, and can be safely and effectively used as a vaccine for hepatitis B. Moreover, the antigen of the present invention can be mass-produced economically and safely. Further, due to its specific antigenicity, the antigen of the present invention can be advantageously utilized as a diagnostic reagent for anti-hepatitis B virus antibodies, and can also be utilized for the preparation of anti-hepatitis B virus antibodies.

It is known that the infection with hepatitis B virus causes acute or chronic hepatitis B, and hepatocirrhosis and liver cancer which are often caused intercurrently with chronic hepatitis B. A large number of patients suffering from hepatitis B exist in Southeast Asia and the central region of Africa, and latent patients carrying hepatitis B virus, such as incubatory carriers and persons who received inapparent infection, are spread all over the world. It is estimated that the number of the patients in the world reaches about 200 millions, and that the number of the latent patients in Japan is about 3 millions, which is about 2.5% of the population of Japan. In other words, hepatitis B is an infectious disease of great importance not only in Japan but also in the countries all over the world and, therefore, the prevention, early diagnosis and early treatment of the disease is a matter of global importance.

The complete particle of hepatitis B virus is called Dane particle. The particle is as large as about 42 nm in diameter and the surface thereof is covered with an HBs antigen. Under the surface, the particle has a core of about 27 nm in diameter. In the core, there are a circular DNA of which the main portion has a double-stranded structure but the remaining small portion has a single-stranded structure, and a DNA polymerase. The length of the circular DNA is of about 3200 base pairs when the single-stranded portion of the circular DNA is artificially repaired so that the single-stranded portion becomes double-stranded and the circular DNA becomes a completely double-stranded DNA. An HBs antigen is a polypeptide of 226 amino acids and the molecular weight thereof is about $2.3 \times 10^4$ dalton. Some of the HBs antigens in the natural state are considered to have a polypeptide called PreS linked thereto at its N-terminus. A PreS comprises 163 amino acids. From the viewpoints of diagnosis and epidemiology, the HBs antigens are roughly classified into four types, namely, adr, adw, ayr and ayw types. It is known that in the Asian countries including Japan, the adr type is prevailing and in the European countries, the adw type.

For preventing infection with hapatitis B, it is necessary to use an HBs antigen as a vaccine. The HBs antigen is obtained from a hapatitis B virus (hereinafter often referred to as "HBV"). To obtain HBs antigen, HBV must be proliferated. The HBV can proliferate only in the bodies of human and chimpanzees because the host range of HBV is limited to human and chimpanzees. However, human bodies cannot be used as a host for proliferating HBV. With respect to chimpanzees also, it is extremely difficult to use chimpanzees as a host because the number of chimpanzees is limited and the import of the chimpanzees is extremely limited from the standpoint of preservation of the chimpanzees. Further, a method for proliferating HBV in a cell culture of a cell line derived from human or chimpanzee is not useful because the HBV cannot proliferate in the cells of a cell line on a large scale. For these reasons, an HBs antigen has conventionally been produced by isolating the virus particles from the blood of a human silent carrier carrying a high concentration of hepatitis B virus particles and purifying the isolated virus particles by centrifugation, salting-out, etc. However, since the supply of the above-mentioned blood is limited, the HBs antigen has not been able to be produced on such a large scale as to meet the global demand. As a result, the HBs antigen has been precious and highpriced.

The above-mentioned problem involved in the production of the HBs antigen is well known to those skilled in the art and various attempts have been made to solve the problem. For example, there have been proposed a method in which *Escherichia coli, Bacillus subtilis,* a pseudomonad, a yeast, a mold, or the like is transformed with a recombinant DNA containing a DNA coding for an HBs antigen to obtain a transformant and the HBs antigen is produced by the transformant (see, for example, Japanese Patent Application Laid-Open Specifications Nos. 55-104887, 56-63995, 57-181099, 57-209298, 59-317999, 59-36699, 59-74988 and 60-89431, United Kingdom Patent Application Laid-Open Specification No. 2125047A and Japanese Translation Publication No. 56-501128 of PCT Patent Application No. WO81/00577; a method in which cultured somatic cells are transformed with a recombinant DNA containing a DNA coding for an HBs antigen to obtain a transformant and the HBs antigen is produced by the obtained transformant (see, for example, Japanese Patent Application Laid-Open Specification No. 58-995); a method in which an HBs antigen is produced by culturing cells which are persistently infected with hepatitis B virus (see Japanese Patent Application Laid-Open Specification No. 56-150020); a method in which an HBs antigen is chemically synthesized (see Japanese Patent Application Laid-Open Specification No. 57-136527); and the like. However, all of these methods have disadvantages or defects with respect to the yield, immunogenicity and quality of the HBs antigen produced. Therefore, none of these methods have been put into practical use.

The present inventors have made extensive and intensive studies with a view to solving the above-mentioned problems. That is, the present inventors have carried out cloning of a DNA coding for an HBs antigen, which is capable of preventing the infection with HBV, and PreS. Further, the present inventors have determined the base sequence of the DNA obtained by the cloning. Then, utilizing the cloned DNA, the present inventors have made studies with respect to the production, by recombinant DNA technique, of an excellent quality antigen which can be effectively and safely used as a vaccine for hepatitis B and can be produced economically and stably in high yield. As a result, the present inventors have found that an antigen comprising an amino acid sequence of an HBs antigen and, linked thereto at its N-terminus, a specific sequence of 9 amino acids derived from the PreS and a methionine in this order has a good quality and excellent immunogenicity and antigenicity as a vaccine for hepatitis B, and can be produced safely and stably on a large scale at low cost. Based on the above-mentioned finding, the present invention has been completed.

Therefore, it is an object of the present invention to provide an antigen which is excellent not only in immunogenicity and antigenicity when used as a vaccine for hepatitis B but also in quality.

It is another object of the present invention to provide a process for producing an antigen of the kind as mentioned above.

It is still another object of the present invention to provide a vaccine comprising an immunogenically effective amount of an antigen of the kind as mentioned above.

The foregoing and other objects, features and advantages of the present invention will be apparent from the following detailed description and appended claims taken in connection with the accompanying drawings in which:

FIG. 3 shows the base sequences of part of plasmid pBH103-ME5 and part of plasmid pBH103-CT and the amino acid sequences of the antigen of the present invention and an HBs antigen (SEQ ID Nos. 1-4)

Figure 1:
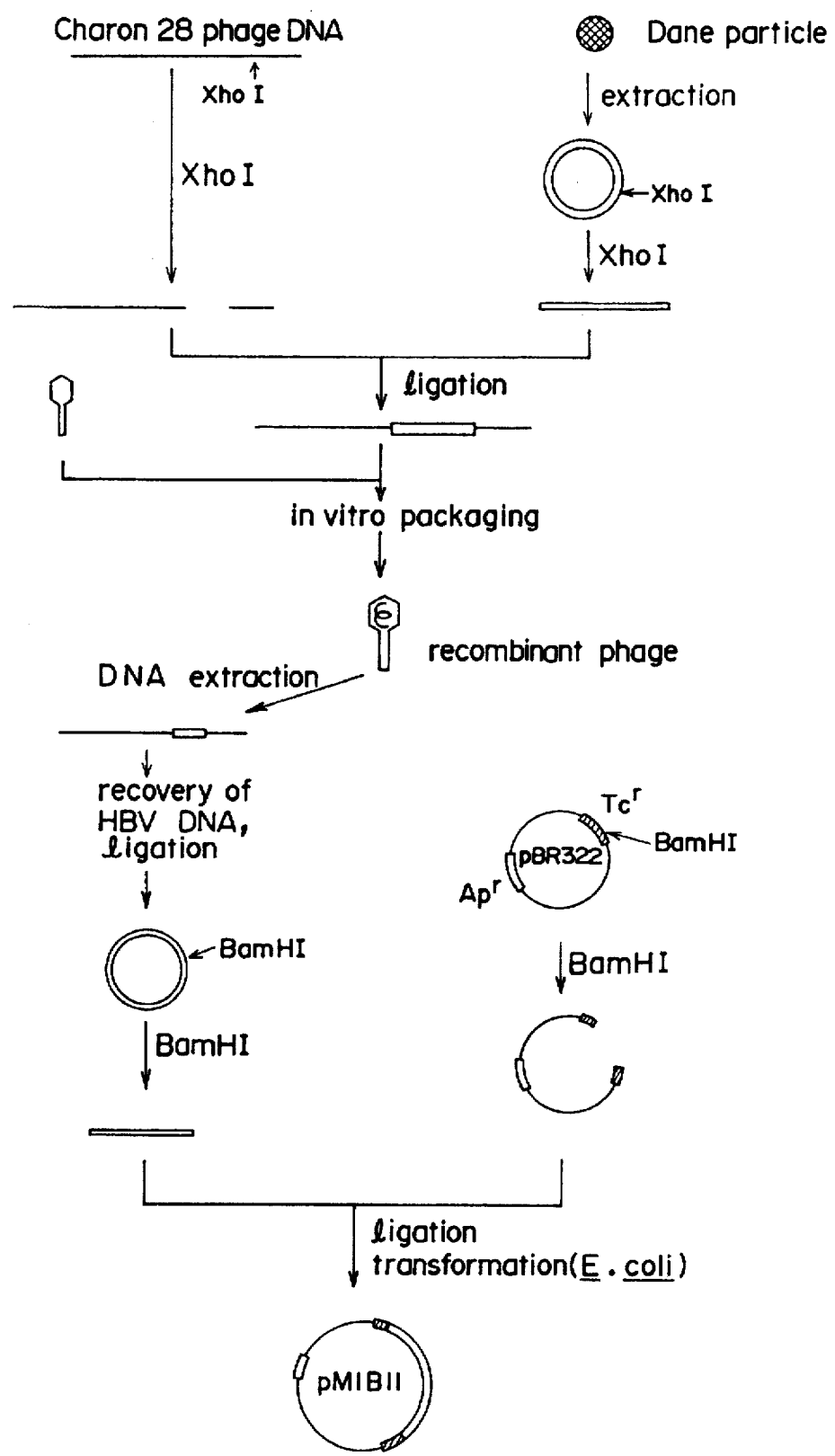
FIG. 1 shows a flow chart indicating the cloning of HBV DNA and preparation of pM1B11.

Essentially, according to the present invention, there is provided a hepatitis B virus antigen comprising an amino acid sequence represented by the following formula (I) (SEQ ID No. 1):

| Met | Ser | Arg | Thr | Gly | Asp | Pro | Ala | Pro | Asn |
|-----|-----|-----|-----|-----|-----|-----|-----|-----|-----|
| Met | Glu | Asn | Thr | Thr | Ser | Gly | Phe | Leu | Gly |
| Pro | Leu | Leu | Val | Leu | Gln | Ala | Gly | Phe | Phe |
| Leu | Leu | Thr | Arg | Ile | Leu | Thr | Ile | Pro | Gln |
| Ser | Leu | Asp | Ser | Trp | Trp | Thr | Ser | Leu | Asn |
| Phe | Leu | Gly | Gly | ala | Pro | Thr | Cys | Pro | Gly |
| Gln | Asn | Ser | Gln | Ser | Pro | Thr | Ser | Asn | His |
| Ser | Pro | Thr | Ser | Cys | Pro | Pro | Ile | Cys | Pro |
| Gly | Tyr | Arg | Trp | Met | Cys | Leu | Arg | Arg | Phe |
| Ile | Ile | Phe | Leu | Phe | Ile | Leu | Leu | Leu | Cys |
| Leu | Ile | Phe | Leu | Leu | Val | Leu | Leu | Asp | Tyr |
| Gln | Gly | Met | Leu | Pro | Val | Cys | Pro | Leu | Leu |
| Pro | Gly | Thr | Ser | Thr | Thr | Ser | Thr | Gly | Pro |
| Cys | Lys | Thr | Cys | Thr | Ile | Pro | Ala | Gln | Gly |
| Thr | Ser | Met | Phe | Pro | Ser | Cys | Cys | Cys | Thr |
| Lys | Pro | Ser | Asp | Gly | Asn | Cys | Thr | Cys | Ile |
| Pro | Ile | Pro | Ser | Ser | Trp | Ala | Phe | Ala | Arg |
| Phe | Leu | Trp | Glu | Trp | Ala | Ser | Val | Arg | Phe |
| Ser | Trp | Leu | Ser | Leu | Leu | Val | Pro | Phe | Val |
| Gln | Trp | Phe | Val | Gly | Leu | Ser | Pro | Thr | Val |
| Trp | Leu | Ser | Val | Ile | Trp | Met | Met | Trp | Tyr |
| Trp | Gly | Pro | Ser | Leu | Tyr | Asn | Ile | Leu | Ser |
| Pro | Phe | Leu | Pro | Leu | Leu | Pro | Ile | Phe | Phe |
| Cys | Leu | Trp | Val | Tyr | Ile |     |     |     |     |
| ..... (I). |

Wherein Ala stands for an alanine residue, Arg an arginine residue, Asn an asparagine residue, Asp an aspartic acid residue, Cys a cysteine residue, Gln a glutamine residue, Glu a glutamic acid residue, Gly a glycine residue, His a histidine residue, Ile an isoleucine residue, Lys a lysine residue, Leu a leucine residue, Met a methionine residue, Phe a phenylalanine residue, Pro a proline residue, Ser a serine residue, Thr a threonine residue, Trp a tryptophan residue, Tyr a tyrosine residue, and Val a valine residue.

Also, according to the present invention, there is provided a deoxyribonucleic acid which comprises a base sequence coding for a hepatitis B virus antigen comprising an amino acid sequence represented by the above-mentioned formula (I).

Further, according to the present invention, there is provided a process for producing a hepatitis B virus antigen comprising an amino acid sequence represented by the above-mentioned formula (I), which comprises:

(a) ligating a deoxyribonucleic acid comprising a base sequence coding for said antigen to a replicable expression vector to obtain a replicable recombinant DNA comprising said deoxyribonucleic acid and said replicable expression vector;

(b) transforming cells of a microorganism or cell culture with said replicable recombinant DNA to form transformants;

(c) selecting said transformants from parent cells of the microorganism or cell culture;

(d) incubating said transformants, causing said transformants to express said deoxyribonucleic acid and produce an antigen; and (e) isolating said antigen from the incubated transformants.

Furthermore, according to the present invention, there is provided a vaccine comprising an immunogenically effective amount of a human hepatitis B virus antigen comprising an amino acid sequence represented by the above-mentioned formula (I).

An HBV antigen according to the present invention comprises the amino acid sequence represented by the above-mentioned formula (I). The amino acid sequence of the formula (I) contains a sequence of 226 amino acids which corresponds to the entire amino acid sequence of an HBs antigen and, ligated thereto at its N-terminus, a sequence of 9 amino acids which is part of the PreS, and a methionine in this order. The PreS is a presequence of the HBs antigen as mentioned before. The sequence of the 9 amino acids is same as the C-terminal amino acid sequence of the PreS.

The antigen of the present invention comprising an amino acid sequence represented by the formula (I) may be prepared and identified by a process comprising steps of (1) to (11) as mentioned below.

In the step (1), Dane particles (complete HBV particles) are isolated from blood and purified. As the blood to be used for isolation of Dane particles, HBe antigen-positive blood may preferably be employed rather than HBs antigen-positive blood. The reason for this is as follows. The HBs antigen is inherently present on the surface of the Dane particle, but often liberated from the Dane particle and present in blood in a state independent of the surface of the Dane particle. Therefore, even if a certain blood sample collected is HBs antigen-positive, the blood sample does not always contain the Dane particle. By contrast, the HBe antigen is present in the core of the Dane particle and is never liberated from the Dane particle. Therefore, if a certain blood sample collected is HBe antigen-positive, such a blood sample always contains the Dane particle. In this step, conventional customary techniques such as ultracentrifugation and the like may be used for the isolation and purification of Dane particles.

In the step (2), HBV DNA is repaired with the endogenous DNA polymerase and recovered. The HBV DNA is of a circular shape and large part of the HBV DNA is inherently double-stranded, but the remaining small part is inherently single-stranded. The single-stranded portion is repaired by customary techniques so that the HBV DNA has a completely double-stranded structure. For this purpose, the DNA polymerase inherent in the HBV particles may be utilized. The DNA repaired may be extracted and recovered by customary techniques such as phenol extraction technique and the like.

In the step (3), the HBV DNA is cloned. As a vector for the cloning, there may be used any known vectors such as plasmids having adaptability to a prokaryotic cell such as *Escherichia coli, Bacillus subtilis* and the like and vectors derived from λ phage and T4 phages. In this step, it is desirable that a suitable combination of a cloning vector and a host cell be selected. The detection and identification of the cloned HBV DNA may be effected by conventional customary methods such as plaque hybridization and Southern blot hybridization. A probe to be used for the detection and identification may be prepared by conventional customary methods, for example, the method employed in Step 2 of Example 1 given later. In practicing the procedure in this step, the following should be noted. Generally, the amount of the HBV DNA recovered in the preceding step (2) is extremely small. Therefore, it is preferred that first, using a phage vectors having high cloning ability, cloning of the HBV DNA is conducted and, subsequently, the thus cloned HBV DNA is further cloned using a plasmid vector.

In the step (4), the HBV DNA is ligated to a replicable expression vector to obtain a recombinant DNA. As a replicable expression vector used in this step, there may be mentioned any known vectors such as expression plasmids, expression shuttle vectors, expression vectors derived from viruses such as vaccinia virus and SV 40, and the like, which have adaptabiliy to host cells to be used. With respect to a host cell, an explanation will be given later.

The ligation of the HBV DNA to a replicable expression vector may be effected by a customary method. In practicing the ligation, it should particularly be noted that the recombinant DNA which is capable of expressing the HBV DNA to produce an antigen having a desired antigencity and immunogenicity in a host may not be obtained by directly ligating the HBV DNA to a replicable expression vector simply. Therefore, in accordance with a customary technique, an expression vector to which the HBV DNA is to be ligated may be modified, in order that:

(i) the production amount of the antigen may be increased as much as possible;

(ii) the antigencity and immunogenicity of an expression product (the antigen) may be increased;

(iii) the stability of the HBV DNA in an expression vector and a host cell may be increased;

(iv) the antigen produced by gene expression in a host cell may be secreted out of the host cell so that the extraction and purification of the antigen can be simplified;

(v) the HBV antigen produced by gene expression may be prevented from being decomposed by the action of a proteolytic enzyme in the cell; and (vi) the culturing conditions of a transformant may be simplified in order to facilitate the culturing.

The above-mentioned modification of an expression vector may be conducted as follows. That is, to an expression vector, DNA's which have an ability to attain the effects mentioned in the above items (i) to (vi) are ligated alone or in combination. As such DNA's, there may be mentioned, for example, an autonomous replication sequence (ARS) or origin of replication (ORI) which is excellent in ability to replicate an expression vector, a promoter excellent in power of gene expression, a DNA coding for a peptide which is capable of enhancing the immunogenicity and antigenicity of the present antigen, a DNA containing a gene for stabilization of a vector, a DNA coding for a signal peptide, etc.

In the step (5), a host cell is transformed by a recombinant DNA obtained in the above-mentioned step (4), and the transformant is isolated.

In this step, trnasformation of a host cell with the recombinant DNA is effected by a customary method such as alkali cation method. As examples of the host cells, there may be mentioned prokaryotic cells such as *Escherichia coli* and *Bacillus subtilis*, and eukaryotic cells such as a yeast and a higher organism cell culture.

The transformants formed by the transformation are selected and isolated from parent cells which remain untransformed with the recombinant DNA, using as a criterion, for example, a phenotypical trait such as drug resistance and auxotrophy of the transformants which is imparted by the replicable expression vector.

In the step (6), the transformant is cultured and the antigen is extracted. In this step, the transformant is cultured by conventional customary methods to express the HBV DNA and produce the antigen. In order to increase the amount of the antigen produced and to stabilize the antigen, the composition of a culture medium, culturing conditions and subculture of transformants may be appropriately selected. For the extraction of the antigen, conventional customary methods, such as physical disruption of the cells, may be employed.

In the step (7), the amount of the antigen in the extract produced by the transformant is determined. The amount of the produced antigen contained in the extract obtained in the step (6) can be measured by conventional customary methods, such as the method in which a commercially available kit for determining an amount of HBs antigen is used.

In the step (8), the base sequence of the HBV antigen structural gene is determined. In this step, the expression vector is extracted from the transformant which exhibits an HBs antigen activity. Then, the HBV DNA gene ligated to the vector is separated from the vector and the base sequence of the HBV DNA is determined. The determination of the base sequence may be effected by conventional customary methods, for example, dideoxy chain termination method and the like.

As a result of the determination of the base sequence of the HBV DNA, the DNA coding for the antigen obtained by the process mentioned above was found to have a base sequence of the following formula (II), nucleotides 138–845 of SEQ ID No. 2:

| | | | | | | | | | |
|---|---|---|---|---|---|---|---|---|---|
| ATG | TCG | AGG | ACT | GGG | GAC | CCT | GCA | CCG | AAC |
| ATG | GAG | AAC | ACA | ACA | TCA | GGA | TTC | CTA | GGA |
| CCC | CTG | CTC | GTG | TTA | CAG | GCG | GGG | TTT | TTC |
| TTG | TTG | ACA | AGA | ATC | CTC | ACA | ATA | CCA | CAG |
| AGT | CTA | GAC | TCG | TGG | TGG | ACT | TCT | CTC | AAT |
| TTT | CTA | GGG | GGA | GCA | CCC | ACG | TGT | CCT | GGC |
| CAA | AAT | TCG | CAG | TCC | CCA | ACC | TCC | AAT | CAC |
| TCA | CCA | ACC | TCT | TGT | CCT | CCA | ATT | TGT | CCT |
| GGC | TAT | CGC | TGG | ATG | TGT | CTG | CGG | CGT | TTT |
| ATC | ATA | TTC | CTC | TTC | ATC | CTG | CTG | CTA | TGC |
| CTC | ATC | TTC | TTG | TTG | GTT | CTT | CTG | GAC | TAC |
| CAA | GGT | ATG | TTG | CCC | GTT | TGT | CCT | CTA | CTT |
| CCA | GGA | ACA | TCA | ACT | ACC | AGC | ACG | GGA | CCA |
| TGC | AAG | ACC | TGC | ACG | ATT | CCT | GCT | CAA | GGA |
| ACC | TCT | ATG | TTT | CCC | TCT | TGT | TGC | TGT | ACA |
| AAA | CCT | TCG | GAC | GGA | AAC | TGC | ACT | TGT | ATT |

```
CCC ATC CCA TCA TCC TGG GCT TTC GCA AGA
TTC CTA TGG GAG TGG GCC TCA GTC CGT TTC
TCC TGG CTC AGT TTA CTA GTG CCA TTT GTT
CAG TGG TTC GTA GGG CTT TCC CCC ACT GTT
TGG CTT TCA GTT ATA TGG ATG ATG TGG TAT
TGG GGG CCA AGT CTG TAC AAC ATC TTG AGT
CCC TTT TTA CCG CTA TTA CCA ATT TTC TTT
TGT CTT TGG GTA TAC ATT
.....(ii)
``` wherein A represents a deoxyadenylic acid residue, G a deoxyguanylic acid residue, C a deoxycytidylic acid residue and T a deoxythymidylic acid redidue, and the left and right ends of formula (II) represent the 5'-hydroxyl group side and 3'-hydroxyl group side, respectively.

The base sequence represented by the above-mentioned formula (II) codes for an amino acid sequence represented by the formula (I) mentioned before.

In the step (9), the HBV antigen produced by expression is isolated from the extract obtained in the above step (6) by customary extraction and purification methods.

In this step, conventional techniques may be used in combination. For example, various techniques such as filtration, salting-out, centrifugation and column chromatography may be used in combination for extracting and purifying the present antigen.

Thus, there is obtained a hepatitis B virus antigen of the present invention comprising an amino acid sequence represented by the above-mentioned formula (I) in substantially pure form.

In the step (10), the molecular weight of the HBV antigen produced is determined, and the antigen is identified. The measurement of the molecular weight of the antigen may be carried out by conventional customary methods, such as SDS-polyacrylamide gel electrophoresis, ultracentrifugal analysis, membrane osmometry, gel filtration and the like. The identification of the antigen may be carried out by a customary method utilizing antigencity as the criterion, for example, a method of gel diffusion precipitation reaction, radioimmunoassay (RIA), enzyme-linked immunosorbent assay (ELISA), reversed passive haemagglutination, passive haemagglutination, immunoadherence haemagglutination, immunoelectrophoresis and the like. It is preferred that the identification of HBV antigen be conducted by employing, in combination, two or more methods from the standpoint of accuracy in identification.

In the step (11), the immunogenicity of the HBV antigen produced is assayed. In accordance with "Minimum Requirements for Biological Products" (Notification No. 159, the Ministry of Health and Welfare), a titration test is conducted using a mouse, a guinea pig, etc.

As mentioned above, the HBV antigen of the present invention may be produced by recombinant DNA technique using a DNA coding for the HBV antigen having an amino acid sequence represented by the formula (I). That is, the present HBV antigen may be produced by a method comprising:

(a) ligating a DNA comprising a base sequence coding for the HBV antigen to a replicable expression vector to obtain a replicable recombinant DNA comprising said deoxyribonucleic acid and said replicable expression vector;

(b) transforming cells of a microorganism or cell culture with said replicable recombinant DNA to form transformants;

(c) selecting said transformants from parent cells of the microorganism or cell culture;

(d) incubating said transformants, causing said transformants to express said deoxyribonucleic acid and produce an antigen; and (e) isolating the antigen from the incubated transformants.

As a DNA comprising a base sequence coding for the HBV antigen, there may be employed the above-mentioned DNA comprising a base sequence represented by the formula (II).

In accordance with degeneracy of genetic code, it is possible to substitute at least one base of the base sequence of a gene by another kind of base without causing the amino acid sequence of the polypeptide produced from the gene to be changed. Hence, the HBV DNA may also have any base sequence that has been changed by substitution in accordance with degeneracy of genetic code. In this instance, the amino acid sequence deduced from the base sequence obtained by the above-mentioned substitution is identical with the amino acid sequence of the formula (I) as defined before. The DNA having the base sequence of the formula (II) can be obtained by repeating the above-mentioned steps (1) to (6) through cloning. Alternatively, a part or whole of the DNA may be organo-chemically synthesized using a commercially available automatic DNA synthesizer etc.

As the host and replicable expression vector to be used for producing the HBV antigen of the present invention by recombinant DNA technique, those which are mentioned, above with respect to the steps (4) and (5) may be employed.

The antigen of the present invention may also be obtained in the form of a fused peptide comprising the amino acid sequence of the HBV antigen and, linked thereto at its C-terminus and/or N-terminus, the amino acid sequence of other peptide such as a peptide derived from an expression vector, peptide derived from a linker, peptide derived from PreS having an amino acid sequence other than the C-terminal amino acid sequence of 9 amino acids and/or peptide derived from the other structural protein of the HBV than the HBs antigen and PreS. In this case, those peptides may be cleaved chemically or enzymatically to separate into the amino acid sequence of HBV antigen and the amino acid sequence of the other peptide which has been linked to the HBV antigen. Alternatively, those fused peptides as such may be used as an antigen if the antigencity is not affected by the presence of the other peptide than the HBV antigen.

The antigen of the present invention may also be organo-chemically synthesized using a commercially available automatic peptide synthesizer etc. Further, the re-designing, synthesis and modification of the antigen of the present invention may be readily effected according to a known customary method of protein engineering.

The antigen of the present invention may be used as an active constituent of a vaccine for hepatitis B. The vaccine may be prepared by adding the antigen of the present invention to a sterilized isotonic solution such as physiological saline or phosphate buffer. In this case, it is preferred that a peptone, amino acid, saccharide or the like be incorporated as a stabilizer in the vaccine. It is possible to previously fix the present antigen with formalin. The vaccine thus obtained is in a liquid form. But the vaccine may be reformulated into an adsorbed vaccine or liposome vaccine by adding an adjuvant or using an artificial phospholipid-membrane for enhancing immunogenicity, or into a lyophilized vaccine which is highly stable and convenient for transportation. The vaccine containing the present antigen may be formulated in the form of mixed vaccines with other vaccines in order to reduce the cost and labor for administration. Further, the immunogenicity of the antigen of the present invention may be enhanced, for example, by introducing a saccharide chain or the like to the antigen by the molecular fusion technique or by modification in the cell after the translation.

The vaccine containing the present antigen may generally be administered in the form of a liquid or suspension. In the case where the vaccine is a lyophilized vaccine, the vaccine is dissolved or suspended in the above-mentioned sterilized isotonic solution before administration. The concentration of the present antigen in the vaccine for administration may generally be about 0.001 to 1000 µg/ml. Generally, the vaccine may be administered subcutaneously or intramuscularly. The dose of the vaccine per adult may generally be in the range of from 0.1 to 2.0 ml. In general, the dose of the vaccine per child may be half as much as that of the vaccine per adult. The vaccine may generally be administered twice at an interval of about one week to one month and then, about half a year later, administered once more.

The antigen of the present invention may also be used as an immunological diagnostic for detecting infections from hepatitis B virus and for determining whether or not patients suffer from hepatitis. For example, the antigen of the present inventon is useful for use in ELISA, reverse passive hemagglutination reaction test and other various tests in which an antigen or antibody labelled with a fluorescent pigment, an enzyme, a radioisotope, etc. are respectively used.

The antigen of the present invention may be used for detecting and identifying an anti-HBV antibody using the above-mentioned various test methods.

The antigen of the present invention may also be used for producing an antibody against the present antigen. The thus produced antibody may be advantageously used for detecting and identifying an HBV antigen using the above-mentioned test methods. The production of such an antibody may be effected by a method in which the antigen of the present invention is injected into a laboratory animal to cause the animal to produce an antibody and then the blood or body fluid of the animal is collected. The antibody may also be produced by a customary cell fusion technique. When the antibody is produced by the former method, there is obtained a polyclonal antibody. On the other hand, when the antibody is produced by the latter method, there is obtained a monoclonal antibody.

Furthermore, the antigen of the present invention or the antibody against the present antigen may be used as a bioseparator, bioreactor and biosenser utilizing the antigen-antibody reaction. In this case, the antigen of the present invention or the antibody against the present antigen may be fixed onto a substrate or support according to a known customary method. In accordance with the purpose, the antigen of the present invention and the antibody against the present antigen may be labelled with a fluorescent pigment, an enzyme, a radioisotope or the like according to a known customary method.

The antigen of the present invention has the following advantages.

The molecular structure of the present antigen is clear. Hence, by the use of the present antigen, it is possible to provide highly effective, highly safe, uniform biological preparations such as a vaccine and highly specific, highly effective diagnostics. Further, the present antigen is not produced by the infection of an animal with a virus, but produced by gene expression of the DNA coding for the present antigen in a host cell. Hence, the possibility of biohazard during the steps of production of the present antigen is substantially eliminated. Also, the production cost can be decreased. Moreover, since all of the materials, e.g. medium of the incubation system are known in respect of the composition and construction thereof, purification is facile and an antigen product having a high purity can be obtained.

The present invention will now be described in detail with reference to the following Examples, which should not be construed to be limiting the scope of the present invention.

EXAMPLE 1

Step 1 [Purification of Dane particles (HBV particles)]

From outpatients suffering from hepatitis, blood samples were collected and pooled. From the pooled blood, serum was obtained and subjected to assay using an RIA kit manufactured and sold by Abott Co., U.S.A. to determine whether or not the serum was HBe antigen-positive. The HBe antigen-positive serum was collected. The serum was subjected to centrifugation at 10,000 rpm at 5° C. for 10 min, and a supernatant was collected. Subsequently, the supernatant was subjected to centrifugation at 28,000 rpm and 5° C. for 4 hours to precipitate Dane particles. The Dane particles were collected and suspended in 10 ml of TNEMEBSA buffer [0.01M Tris-HCl (pH 7.5), 0.1M NaCl, 0.001M EDTA, 0.1% (w/w) 2-mercaptoethanol and 1 mg/ml bovine serum albumin]. The thus obtained suspension was layered over a 30% sucrose containing TNEMEBSA put in a centrifuge tube, and subjected to centrifugation at 40,000 rpm at 5° C. for 13 hours to obtain precipitates. The resultant precipitates were suspended in 400 µl of TNEME buffer (the same buffer as the above-mentioned TNEMEBSA buffer except that the bovine serum albumin was not contained), thereby to obtain a purified Dane particle suspension.

Step 2 [Recovery of HBV DNA repaired with the endogenous DNA polymerase]

To 50 µl of the purified Dane particle suspension were added 1.50 µl of TE [10 mM Tris-HCl (pH 8.0) and 0.1 mM EDTA] and 100 µl of a solution [0.33M Tris-HCl (pH 8.0), 0.125M $MgCl_2$, 0.4M $NH_4Cl$, 0.4%(w/w) NP-40, 0.5%(w/w) 2-mercaptoethanol, 2 mM dATP, 2 mM dTTP, 0.5 mM dCTP, 0.5 mM dGTP, 3 µM α[$^{32}$P]dCTP and 3 µM α[$^{32}$P]dGTP]. The resulting mixture was allowed to react at 37° C. for 2 hours. Subsequently, 7.5 µl each of 10 mM dCTP and 10 mM dGTP were added to the mixture, and allowed to react at 37° C. for 3 hours, thereby to repair the single-stranded portion in the HBV DNA by the action of the endogenous DNA polymerase present in the Dane particles. Thus, there was obtained a mixture which contained Dane particles containing a [$^{32}$P]-labeled HBV DNA having a completely double-stranded structure. Then, 30 µl of 0.5M EDTA (pH 8.0), 100 µl of 5 mg/ml of protease K and 50 µl of 10% (w/w) sodium dodecyl sulfate (SDS) was added to the above-obtained mixture, and the mixture was allowed to react at 56° C. for 2 hours. Then, the mixture was subjected to extraction three times with 550 µl of water-saturated phenol to obtain an extract. The extract was applied to a column packed with Sephadex G-50 (manufactured and sold by Pharmacia Chemicals AB, Sweden) and the void fraction was collected. The thus obtained fraction contained [$^{32}$P]-labeled HBV DNA.

Step 3 [Cloning of HBWDNA]

An aliquot of the fraction containing the HBV DNA obtained in Step 2 was subjected to digestion with various restriction enzymes to analyze the restriction endonuclease cleavage sites of the DNA. As a result, it was found that the HBV DNA had one XhoI site and one BamHI site as restriction endonuclease cleavage sites. Utilizing these endonuclease cleavage sites, the HBV DNA was cloned in a manner as described hereinbelow.

(A) Cloning at XhoI site of λ phage Charon 28

Substantially the same procedures as in Step 2 except that the labelled dCTP and dGTP were not used were repeated to obtain a fraction containing the HBV DNA. The fraction was subjected to ethanol precipitation to form HBV DNA precipitates. The precipitates were collected and dissolved in 50

μl of a mixture of 10 mM Tris-HCl, 7 mM MgCl$_2$, 100 mM NaCl and 7 mM 2-mercaptoethanol. To the thus obtained solution was added a restriction enzyme XhoI, followed by incubation at 37° C. for 1 hour to cleave the HBV DNA by the restriction enzyme XhoI. After the cleavage, the mixture was subjected to extraction with an equi-volume of water-saturated phenol. To the resulting extract were added a 2-fold volume of cold ethanol and a 1/10 volume of 3M potassium acetate (pH4.8), and the resulting mixture was allowed to stand at -20° C. for 1 hour so that DNA precipitated. Then, the mixture was subjected to centrifugation at 10000 rpm for 10 min to collect the XhoI-cleaved HBV DNA.

In substantially the same manner as mentioned above, λ phage Charon 28 DNA (having one XhoI site) (manufactured and sold by Bethesda Research Laboratories Inc., U.S.A.) was cleaved by XhoI. The resulting cleaved λ phage Charon 28 DNA was mixed with the above-obtained XhoI-cleaved HBV DNA. The mixture was treated with T4 DNA ligase in a solution containing 67 mM Tris-HCl (pH7.6), 6.7 mM MgCl$_2$, 100 μg/ml of gelatin, 10 mM dithiothreitol and 1 mM ATP at 12° C. for 12 hours. The resulting mixture was subjected to extraction with an equi-volume of water-saturated phenol, followed by ethanol precipitation using a 2-fold volume of ethanol and a 1/10 volume of 3M potassium acetate, thereby to obtain precipitates. The thus obtained precipitates were dissolved in 10 μl of TE buffer to obtain a DNA solution containing a recombinant phage DNA.

Then, using the DNA solution containing the recombinant phage DNA, the in vitro packaging of the recombinant phage DNA was effected by the in vitro packaging method [Methods in Enzymology (1978), 68, 299–309] using a λ-DNA in vitro packaging kit (manufactured and sold by Takara Shuzo Co., Ltd., Japan), thereby to obtain a virus particle. With the thus obtained virus particle, cells of *E. coli* strain DP50$_{sup}$ F were transformed to obtain transformants. The transformants were inoculated on an L agar medium (1 w/v % bactotrypton, 0.5 w/v% yeast extract, 0.5 w/v% sodium chloride, 1.5 w/v% agar, pH7.2–7.4), followed by incubation at 37° C. for 6 hours, thereby to form plaques on the L agar medium. Then, plaque hybridization was carried out using as a probe the $^{32}$P-labelled HBV DNA, which had been obtained in Step 2, by the method as described in Manual for Genetic Engineering, Kodansha Scientific, p.68–73, published on Sep. 20, 1982, thereby to isolate transformants which contained recombinant phages carrying the XhoI-cleaved HBV DNA (FIG. 1).

(B) Re-cloning at BamHI site of plasmid pBR322

Cells of *Escherichia coli* strain DP50$_{sup}$ F were infected with the recombinant phage containing the XhoI-cleaved HBV DNA obtained in the above Substep (A), followed by culturing to multiply the recombinant phage DNA in the cells of the *E. coli* strain by the method as described in Manual for Genetic Engineering, pp. 11–20. Then, from the cells, the recombinant phage DNA was isolated by the rapid alkali extraction method [Necleic Acid Research, 7 (6), 1513–1523 (1979)]. The thus obtained phage DNA was cleaved with XhoI in substantially the same manner as described in Substep (A) mentioned above, and subjected to 1 w/v% low melting point agarose electrophoresis. Since the HBV DNA has a molecular length of about 3.2 kb [Nature, 317, 489–495 (1985)], a gel portion corresponding to a molecular weight of about 3.2 kb was cut off from the gel. To the cut-off gel was added a 5-fold volume of TE buffer, and the mixture was heated to 65° C. to dissolve the gel. The solution was subjected to phenol extraction and ethanol precipitation in the same manner as described in Substep (A), to obtain the HBV DNA which was in a linear form. The thus obtained HBV DNA was subjected to reaction with T4 DNA ligase under the same conditions as described in Substep (A) to form a circular DNA. The resulting reaction mixture was subjected to phenol extraction and ethanol precipitation in the same manner as described above to obtain circular DNA precipitates and the thus obtained circular DNA precipitates were dissolved in a solution containing 10 mM Tris-HCl (pH 8.0), 7 mM MgCl$_2$, 100 mM NaCl, 2 mM 2-mercaptoethanol and 0.01% bovine serum albumin. To the thus obtained circular DNA solution was added a restriction enzyme BamHI to cleave the circular DNA. Then, the mixture containing the resulting DNA was subjected to phenol extraction and ethanol precipitation in substantially the same manner as mentioned above to obtain an HBV DNA both ends of which had been cleaved by BamHI.

Then, the plasmid pBR322 was cleaved with BamHI in substantially the same manner as described above, and the cleaved plasmid pBR322 was mixed with the above-obtained HBV DNA cleaved with BamHI and the mixture was subjected to reaction with T4 DNA ligase under the same conditions as described before, to obtain a recombinant DNA. Using the thus obtained recombinant DNA, cells of *Escherichia coli* X1776 (ATCC 31244) was transformed according to the method described in Molecular Cloning, pp. 254–255(1982), published by Cold Spring Harbor Laboratory, thereby to obtain transformants. The transformants were inoculated on a plate of antibacterial test medium 3 (manufactured and sold by Difco Laboratories, U.S.A.) which contained 25 μg/ml of ampicillin, followed by culturing. Thus, the transformant containing a plasmid pBR322 having HBV DNA inserted to its BamHI site was found to exhibit ampicillin resistance and tetracycline sensitiveness. From the thus obtained transformant, a plasmid DNA was extracted by the method described in the above-mentioned "Molecular Cloning" pp.368–369. The plasmid DNA was cleaved with a restriction enzyme BamHI in substantially the same manner as described above. The resulting cleaved DNA was subjected to Southern blot hybridization by the method as described in the above mentioned "Manual for Genetic Engineering" pp 73–80 using as a probe the $^{32}$P-labelled HBV DNA obtained in Step 2, and it was confirmed that HBV DNA of about 3.2 kb was cloned. The above-obtained plasmid was designated pMIB11 (See FIG. 1). Further, the transformant containing the plasmid pMIB11 was designated *E. coli* X1776/pMIB11 and deposited at the Fermentation Research Institute, Japan under the accession No. FERM BP-1081.

Step 4 [Construction of a plasmid capable of expressing the HBV DNA to produce HBV antigen and modification of the same]

Figure 2:
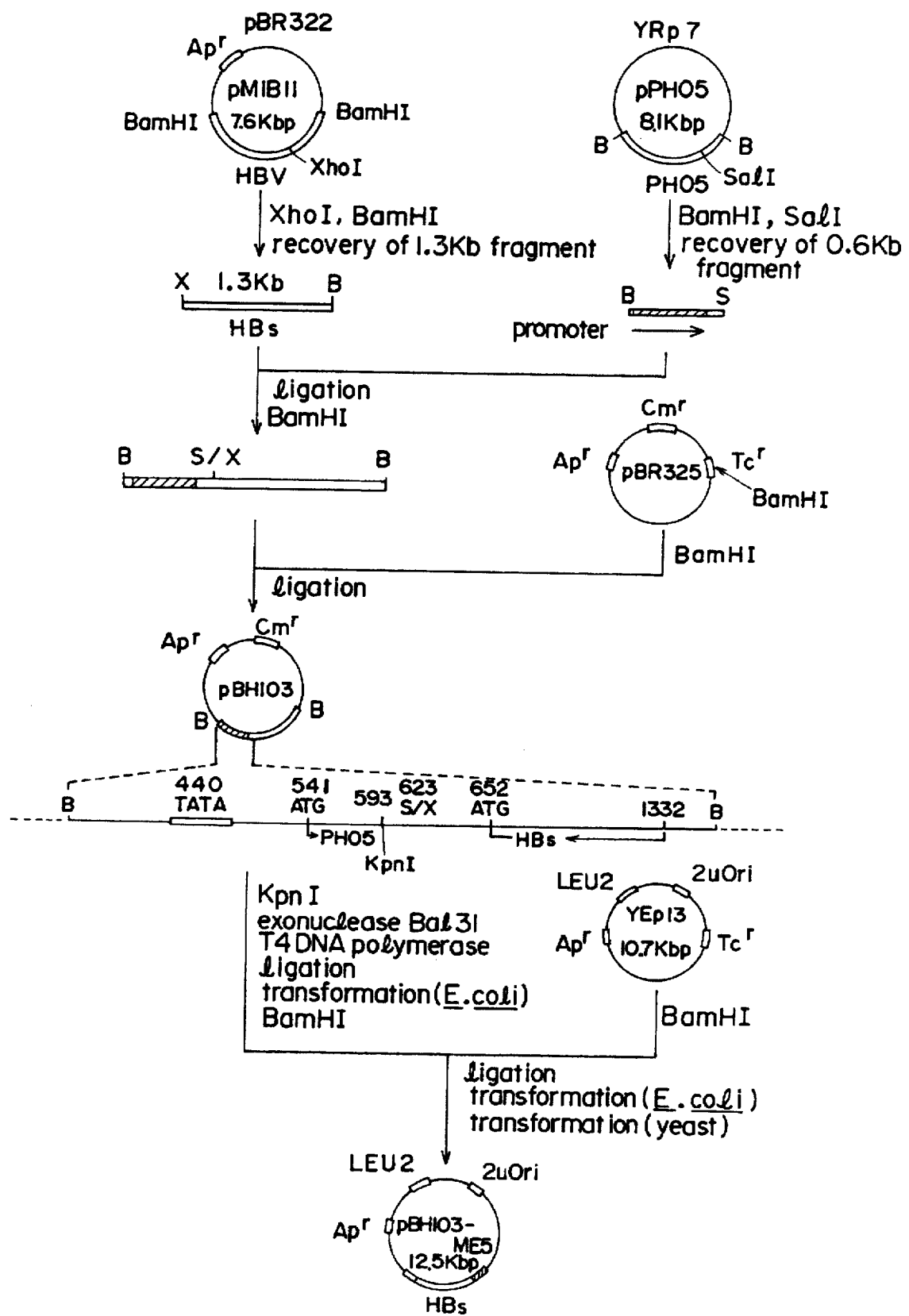
FIG. 2 shows a flow chart indicating the preparation of plasmid pBH103 series.

The plasmid pMIB11 obtained in Step 3 was digested with restriction enzymes XhoI and BamHI to obtain a DNA fragment of about 1.3 kb containing a DNA coding for HBs antigen. On the other hand, plasmid pPHO5 obtained according to the method described in Kenji Arima et al., Nucl. Acid Res., 11, 1657, 1983 was digested with restriction enzymes BamHI and SalI to obtain a DNA fragment of about 0.6 kb containing a PHO5 promoter. Further, the above-obtained two kinds of DNA fragments were ligated to each other by the use of T4 DNA ligase. Then, the ligated DNA was cleaved with restriction enzyme BamHI, to obtain a DNA fragment of 1.9 kb having the PHO5 promoter and a gene Coding for HBs. Then, the thus obtained DNA fragment was mixed with a DNA fragment prepared by digesting plasmid pBR325 with restriction enzyme BamHI and alkali phosphatase, and the resulting mixture was allowed to react with T4 DNA ligase to obtain a plasmid having such a structure that the DNA fragment containing PHO5 and, linked to the downstream thereof, a gene coding for HBs antigen was inserted into the BamHI site of the plasmid pBR325. Then, the resulting plasmid was digested with a restriction enzyme KpnI, and further digested with exonuclease Ba131. Thus, there was obtained a mixture containing plasmid clones void of initiation codon ATG of the structural gene of PHO5, which plasmid clones had various molecular lengths. These plasmid clones in the mixture were digested with restriction enzyme BamHI, and separately inserted into the BamHI site of plasmid YEp13 (ATCC 37115) to obtain a mixture of expression plasmid series. The plasmid series were designated pBH103 series. (see FIG. 2)

Step 5 [Transformation of yeast with the expression plasmid pBH103 series and isolation of a transformed yeast]

Cells of the yeast strain *Saccharomyces cerevisiae* SHY4 (ATCC Accession No. 44772) were transformed with the expression plasmid pBH103 series according to the alkali cation method. Illustratively stated, the yeast was cultured in YPD medium (2 w/v% bactopeptone, 1 w/v% yeast extract, 2 w/v% dextrose), and 5 ml of the culture was centrifuged at 2500 rpm for 5 min to harvest cells. The cells were suspended in 5 ml of TE buffer, and centrifuged at 2500 rpm for 5 min to harvest cells. The cells were resuspended in 0.6 ml of TE buffer to obtain a suspension. To 0.5 ml of the suspension was added 0.5 ml of 0.2M lithium acetate, and incubated at 30° C. for 60 min. Then, to 0.1 ml of the resulting culture was added 7 µl of the above-obtained mixture of expression plasmid series, and incubated at 30° C. for 30 min. To the resulting culture was added 0.1 ml of 70 w/v% polyethylene glycol 4000, and incubated at 30° C. for 60 min. Then, 2 ml of distilled water was added to the culture, followed by centrifugation at 2500 rpm for 5 min to harvest cells. The cells were suspended in a small amount of distilled water and inoculated to an SD agar medium [0.67 w/v% bactoyeast (nitrogen base, amino acid free) (manufactured and sold by Difco Laboratories, U.S.A.), 2 w/v% dextrose, 20 µg/ml uracil, 20 µg/ml L-tryptophan, 20 µg/ml L-histidine, 2 w/v% agar] which was a selective medium not containing leucine. The resulting agar medium was incubated at 30° C. to form colonies. The colonies were isolated to obtain transformed yeasts.

Step 6 [Incubation of the transformed yeasts and extraction of an antigen]

Each of the transformed yeasts obtained in Step 5 was inoculated to a Burkholder medium which is a completely sysnthetic medium containing 1.5 g/l monobasic potassium phosphate, 20 µg/ml uracil, 20 µg/ml L-tryptophan and 20 µg/ml L-histidine (see Burkholder, P. R. et al., Am. J. Botany, 30, 206, 1943), and incubated while shaking at 30° C. for 24 hr. After the incubation, the culture was centrifuged at 2500 rpm for 5 min to harvest cells. The cells were washed with distilled water once, inoculated to a Burkholder medium which contained 1.5 g/l potassium chloride in place of the above-mentioned monobasic potassium phosphate, and incubated while shaking at 30° C. for 24 hr. After the incubation, the cells were harvested by centrifugation, washed and suspended in 50 mM phosphate buffer (pH 7.2). Glass beads (having a diameter of 0.45–0.55 mm) were put in the suspension, and vigorously shaken to disrupt the cells. The resulting suspension was centrifuged at 10,000 rpm for 10 min, to separate into a supernatant and a cell pellet. The supernatant was collected. Thus, there was obtained a yeast extract.

Step 7 [Measurement of the amount of the antigen produced by the transformed yeast]

Quantitative determination of the antigen in the yeast extract obtained in Step 6 was carried out using Auslia II, a commercially available HBs antigen measuring kit (manufactured and sold by Abott Co., U.S.A.). Measurement of the amount of the antigen produced by each of the transformed yeasts obtained in Step 5 showed that one of the yeasts, which has a plasmid designated pBH103-ME5, produced a high amount of the antigen. Also, a yeast having a plasmid designated pBH103-CT exhibited antigen-producing property. The results are shown in Table 1.

TABLE 1

| Plasmid possessed by transformed yeast | Amount of antigen produced by transformed yeast (ng/ml) |
| --- | --- |
| pBH 103-ME5 | 953 |
| pBH 103-CT | 184 |

Step 8 [Determination of DNA base sequences of PHO5 promoter and structural gene coding for the antigen of the plasmid pBH103-ME5]

The plasmid pBH103-ME5 was cleaved with various kinds of restriction enzymes to obtain DNA fragments. The DNA fragments were inserted in a plasmid pUC12 [Messing, J., "Methods in Enzymology", 101, part C, 20 (1983)], followed by determination of the base sequences of the PHO5 promoter and the DNA coding for the antigen carried by the plasmid pBH103-ME5 by the dideoxy chain termination method [Sanger, F., et al., Prec Natl. Acad. Sci, U.S.A., 74, 5463 (1977); Hattori, M. et al, Anal. Biol., 152, 232, (1986)]. The results are shown in FIG. 3.

From the base sequence shown in FIG. 3, it was found that the antigen coded by the structural gene has an amino acid sequence consisting of the sequence of 226 amino acids coding for the HBs antigen and, linked thereto at its N-terminus, a sequence of 9 amino acids corresponding to the C-terminal amino acid sequence of the PreS and a methionine residue derived from an initiation codon ATG (see FIG. 3). The transformed yeast containing the plasmid pBH103-ME5 was designated SHY4/pBH103-ME5 and was deposited with the International Depository of the National Institute of Bioscience and Human Technology (NIBHT) of the Agency of Industrial Science and Technology, 1-3, Higashi 1-chome-Tsukuba-shi, Ibaraki-ken, Japan under accession number FERM BP-5802, under the provisions of the Budapest Treaty.

On the other hand, the base sequences of the promoter PHO5 and the stractural gene coding for the antigen carried by the plasmid pBH103-CT was also determined in substantially the same manner as mentioned above. The results are also shown in FIG. 3. From the base sequence shown in FIG. 3, it was found that the antigen coded by the structural gene carried by the plasmid pBH103-CT has an amino acid sequence consisting of 226 amino acids of the HBs antigen (see FIG. 3). The transformed yeast containing the plasmid pBH103-CT was designated SHY4/pBH103-CT.

Step 9 [Identification and molecular weight determination of the antigen produced by the transformed yeast SHY4/pBH103-ME5]

Figure 4:
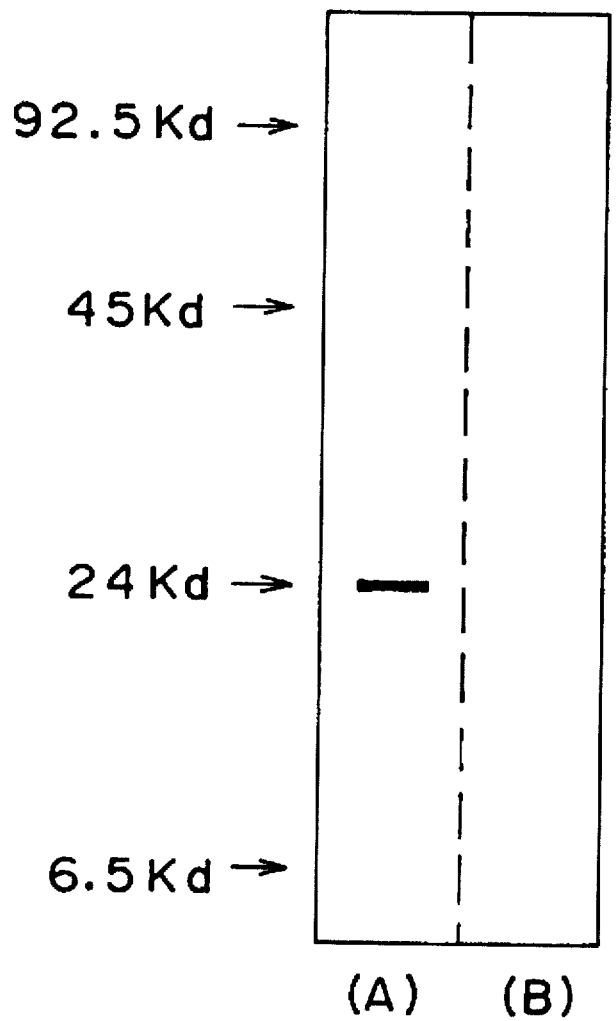
FIG. 4 (lanes A and B) shows the results of SDS-polyacrylamide gel electrophoresis of the antigen of the present invention.

In substantially the same manner as described in Step 6, the transformed yeast SHY4/pBH103-ME5 was cultured and from the resulting culture, an extract was obtained. To the extract was added 2% (w/v) active carbon. The resulting mixture was stirred at room temperature for 30 min, followed by centrifugation at 3000 rpm for 10 min to obtain a supernatant. The supernatant was concentrated by means of ultrafiltration. The resulting concentrate was layered over a sucrose solution having a sucrose density gradient of 20–50% (w/v), followed by centrifugation at 20000 rpm for 20 hr. The thus obtained mixture was fractionated and subjected to determination of the amount of the antigen in substantially the same manner as in Step 7. As a result, it was found that the antigen was contained in a fraction having a sucrose density of about 35%. This fraction was dialyzed against 50 mM phosphate buffer (pH7.2), and to the resulting dialysate was added CsCl in such an amount that the specific gravity of the resulting mixture became 1.2. The mixture was subjected to centrifugation at 42000 rpm for 40 hr. The resulting mixture was fractionated and subjected to determination of the amount of the antigen in substantially the same manner as in Step 7. As a result, it was found that the antigen was contained in a fraction having a specific gravity of 1.21. The thus obtained purified antigen solution was subjected to SDS-polyacrylamide gel electrophoresis. After completion of the electrophoresis, the gel was taken, and the proteins on the gel were blotted onto a nitrocellulose film. The resulting nitrocellulose film was subjected to reaction with an anti-human-HBs goat serum (manufactured and sold by DAKO Co., Ltd., U.S.A.) labelled with horseradish peroxidase (HRPO), followed by color development reaction using 4-chloroindonaphthol for the purpose of detecting the antigen. As a result, there was detected a band of the antigen at the position corresponding to a molecular length of 24 kilodalton (kd) (see FIG. 4). In FIG. 4, the left lane (A) shows the result of electrophoresis of the purified antigen of the present invention, and the right lane (B) shows the result of electrophoresis of a yeast extract obtained from the parent yeast cells (control).

Further, using the anti-human-HBs goat serum (manufactured and sold by DAKO Co., Ltd., U.S.A.), HBs antigen derived form human blood and the above-mentioned purified antigen of the present invention, a precipitation assay was conducted in the following manner. 50 µl of the above-mentioned antiserum, 50 µl of the human blood-derived HBs antigen and 50 µl of the purified antigen of the present invention were separately poured into 3 holes (which were arranged in such a relationship that an imaginary triangle formed by the holes as the vertexes is a regular triangle) on a 0.8% (w/v) agarose gel. The gel was allowed to stand overnight at room temperature. Then, the precipitin lines formed by the reactions between the antigens and antiserum were observed. As a result, it was found that the precipitin line formed by the reaciton between the antiserum and the HBs antigen derived from human blood, and the precipitin line formed by the reaciton between the antiserum and the purified antigen of the present invention were completely fused. This result indicated that the purified antigen of the present invention and the HBs antigen derived from human blood were identical with respect to antigenicity.

Step 10 [Assay of immunogenicity of the antigen produced by the transformed yeast SHY4/pBH103-ME5]

Substantially the same procedures as in Step 9 were repeated to obtain a purified antigen of the present invention. Then, in accordance with the standards for preparing an adsorbed vaccine for hepatitis B recited in "Minimum Requirements for Biological Products" (Notification No. 159 of Ministry of Health and Welfare of Japanese Government), a vaccine for hepatitis B was prepared from the present antigen as follows. The present antigen was dissolved in a physiological saline to obtain a solution containing 40 µg/ml of the above-described purified antigen. To the solution was added an equi-volume of a physiological saline containing 0.4 µg/ml of aluminum hydroxide, followed by mixing. Thus, there was prepared an aluminum-adsorbed vaccine for hepatitis B. 1 ml of the prepared vaccine was subcutaneously inoculated to each of 10 BALB/c mice of 5 weeks old at their backs. 5 weeks after the inoculation, blood samples were collected from the mice, and subjected to passive hemagglutination test to determine the antibody titer in the blood samples. The results are shown in Table 2.

TABLE 2

| Vaccine | relation antigen titer |
|---|---|
| Lot y003[1] | 1.76 |
| Reference product[2] | 1.0 |

[1] vaccine of the present invention
[2] "Reference adsorbed vaccine for hepatitis B" used for titration test obtained from National Institute of Health, Japan.

What is claimed is:

1. A process for producing a hepatitis B virus antigen, comprising:

(a) transforming host cells of yeast strain *Saccharomyces cerevisiae* SHY4 (ATCC Accession Number 44772) with plasmid pBH103-ME5 to form transformant SHY4/pBH103-ME5;

(b) selecting said transformant from parent cells of yeast strain *Saccharomyces cerevisiae* SHY4;

(c) incubating said transformant, causing said transformant to express a hepatitis B virus antigen encoded by a deoxyribonucleic acid of SEQ ID No. 2 contained in said plasmid pBH103-ME5; and (d) isolating said antigen from the incubated transformant.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 236 amino acids
( B ) TYPE: amino acid
( D ) TOPOLOGY: linear ( i i ) MOLECULE TYPE: protein ( x i ) SEQUENCE DESCRIPTION: SEQ ID NO:1:

Met  Ser  Arg  Thr  Gly  Asp  Pro  Ala  Pro  Asn  Met  Glu  Asn  Thr  Thr  Ser
1              5                        10                          15

```
Gly  Phe  Leu  Gly  Pro  Leu  Leu  Val  Leu  Gln  Ala  Gly  Phe  Phe  Leu  Leu
               20                  25                       30

Thr  Arg  Ile  Leu  Thr  Ile  Pro  Gln  Ser  Leu  Asp  Ser  Trp  Trp  Thr  Ser
          35                       40                            45

Leu  Asn  Phe  Leu  Gly  Gly  Ala  Pro  Thr  Cys  Pro  Gly  Gln  Asn  Ser  Gln
     50                  55                       60

Ser  Pro  Thr  Ser  Asn  His  Ser  Pro  Thr  Ser  Cys  Pro  Pro  Ile  Cys  Pro
65                       70                       75                            80

Gly  Tyr  Arg  Trp  Met  Cys  Leu  Arg  Arg  Phe  Ile  Ile  Phe  Leu  Phe  Ile
                    85                       90                            95

Leu  Leu  Leu  Cys  Leu  Ile  Phe  Leu  Leu  Val  Leu  Leu  Asp  Tyr  Gln  Gly
               100                      105                      110

Met  Leu  Pro  Val  Cys  Pro  Leu  Leu  Pro  Gly  Thr  Ser  Thr  Thr  Ser  Thr
               115                      120                      125

Gly  Pro  Cys  Lys  Thr  Cys  Thr  Ile  Pro  Ala  Gln  Gly  Thr  Ser  Met  Phe
               130                 135                      140

Pro  Ser  Cys  Cys  Cys  Thr  Lys  Pro  Ser  Asp  Gly  Asn  Cys  Thr  Cys  Ile
145                      150                      155                           160

Pro  Ile  Pro  Ser  Ser  Trp  Ala  Phe  Ala  Arg  Phe  Leu  Trp  Glu  Trp  Ala
               165                      170                      175

Ser  Val  Arg  Phe  Ser  Trp  Leu  Ser  Leu  Leu  Val  Pro  Phe  Val  Gln  Trp
               180                      185                      190

Phe  Val  Gly  Leu  Ser  Pro  Thr  Val  Trp  Leu  Ser  Val  Ile  Trp  Met  Met
               195                      200                      205

Trp  Tyr  Trp  Gly  Pro  Ser  Leu  Tyr  Asn  Ile  Leu  Ser  Pro  Phe  Leu  Pro
210                           215                      220

Leu  Leu  Pro  Ile  Phe  Phe  Cys  Leu  Trp  Val  Tyr  Ile
225                      230                      235
```

( 2 ) INFORMATION FOR SEQ ID NO:2:

( i ) SEQUENCE CHARACTERISTICS:
    ( A ) LENGTH: 845 base pairs
    ( B ) TYPE: nucleic acid
    ( C ) STRANDEDNESS: single
    ( D ) TOPOLOGY: linear ( i i ) MOLECULE TYPE: cDNA from genomic RNA ( x i ) SEQUENCE DESCRIPTION: SEQ ID NO:2:

```
ATACCCATTT  GGGATAAGGG  TAAACATCTT  TGAATTGTCG  AAATGAAACG  TATATAAGCG         60

CTGATGTTTT  GCTAAGTCGA  GGTTAGTATG  GCTTCATCTC  TCATGAGAAT  AAGAACAACA        120

ACAAATAGAG  CTAGCCG  ATG  TCG  AGG  ACT  GGG  GAC  CCT  GCA  CCG  AAC  ATG  GAG       173
                    Met  Ser  Arg  Thr  Gly  Asp  Pro  Ala  Pro  Asn  Met  Glu
                     1                 5                             10

AAC  ACA  ACA  TCA  GGA  TTC  CTA  GGA  CCC  CTG  CTC  GTG  TTA  CAG  GCG  GGG       221
Asn  Thr  Thr  Ser  Gly  Phe  Leu  Gly  Pro  Leu  Leu  Val  Leu  Gln  Ala  Gly
               15                       20                       25

TTT  TTC  TTG  TTG  ACA  AGA  ATC  CTC  ACA  ATA  CCA  CAG  AGT  CTA  GAC  TCG       269
Phe  Phe  Leu  Leu  Thr  Arg  Ile  Leu  Thr  Ile  Pro  Gln  Ser  Leu  Asp  Ser
     30                       35                       40

TGG  TGG  ACT  TCT  CTC  AAT  TTT  CTA  GGG  GGA  GCA  CCC  ACG  TGT  CCT  GGC       317
Trp  Trp  Thr  Ser  Leu  Asn  Phe  Leu  Gly  Gly  Ala  Pro  Thr  Cys  Pro  Gly
45                       50                       55                           60

CAA  AAT  TCG  CAG  TCC  CCA  ACC  TCC  AAT  CAC  TCA  CCA  ACC  TCT  TGT  CCT       365
Gln  Asn  Ser  Gln  Ser  Pro  Thr  Ser  Asn  His  Ser  Pro  Thr  Ser  Cys  Pro
               65                       70                       75
```

-continued

| | | | | | | | | | | | | | | | |
|---|---|---|---|---|---|---|---|---|---|---|---|---|---|---|---|
| CCA | ATT | TGT | CCT | GGC | TAT | CGC | TGG | ATG | TGT | CTG | CGG | CGT | TTT | ATC | ATA | 413
| Pro | Ile | Cys | Pro | Gly | Tyr | Arg | Trp | Met | Cys | Leu | Arg | Arg | Phe | Ile | Ile |
| | | | 80 | | | | | 85 | | | | | 90 | | |
| TTC | CTC | TTC | ATC | CTG | CTG | CTA | TGC | CTC | ATC | TTC | TTG | TTG | GTT | CTT | CTG | 461
| Phe | Leu | Phe | Ile | Leu | Leu | Leu | Cys | Leu | Ile | Phe | Leu | Leu | Val | Leu | Leu |
| | | 95 | | | | | 100 | | | | | 105 | | | |
| GAC | TAC | CAA | GGT | ATG | TTG | CCC | GTT | TGT | CCT | CTA | CTT | CCA | GGA | ACA | TCA | 509
| Asp | Tyr | Gln | Gly | Met | Leu | Pro | Val | Cys | Pro | Leu | Leu | Pro | Gly | Thr | Ser |
| | 110 | | | | | 115 | | | | | 120 | | | | |
| ACT | ACC | AGC | ACG | GGA | CCA | TGC | AAG | ACC | TGC | ACG | ATT | CCT | GCT | CAA | GGA | 557
| Thr | Thr | Ser | Thr | Gly | Pro | Cys | Lys | Thr | Cys | Thr | Ile | Pro | Ala | Gln | Gly |
| 125 | | | | | 130 | | | | | 135 | | | | | 140 |
| ACC | TCT | ATG | TTT | CCC | TCT | TGT | TGC | TGT | ACA | AAA | CCT | TCG | GAC | GGA | AAC | 605
| Thr | Ser | Met | Phe | Pro | Ser | Cys | Cys | Cys | Thr | Lys | Pro | Ser | Asp | Gly | Asn |
| | | | | 145 | | | | | 150 | | | | | 155 | |
| TGC | ACT | TGT | ATT | CCC | ATC | CCA | TCA | TCC | TGG | GCT | TTC | GCA | AGA | TTC | CTA | 653
| Cys | Thr | Cys | Ile | Pro | Ile | Pro | Ser | Ser | Trp | Ala | Phe | Ala | Arg | Phe | Leu |
| | | | 160 | | | | | 165 | | | | | 170 | | |
| TGG | GAG | TGG | GCC | TCA | GTC | CGT | TTC | TCC | TGG | CTC | AGT | TTA | CTA | GTG | CCA | 701
| Trp | Glu | Trp | Ala | Ser | Val | Arg | Phe | Ser | Trp | Leu | Ser | Leu | Leu | Val | Pro |
| | | 175 | | | | | 180 | | | | | 185 | | | |
| TTT | GTT | CAG | TGG | TTC | GTA | GGG | CTT | TCC | CCC | ACT | GTT | TGG | CTT | TCA | GTT | 749
| Phe | Val | Gln | Trp | Phe | Val | Gly | Leu | Ser | Pro | Thr | Val | Trp | Leu | Ser | Val |
| | 190 | | | | | 195 | | | | | 200 | | | | |
| ATA | TGG | ATG | ATG | TGG | TAT | TGG | GGG | CCA | AGT | CTG | TAC | AAC | ATC | TTG | AGT | 797
| Ile | Trp | Met | Met | Trp | Tyr | Trp | Gly | Pro | Ser | Leu | Tyr | Asn | Ile | Leu | Ser |
| 205 | | | | | 210 | | | | | 215 | | | | | 220 |
| CCC | TTT | TTA | CCG | CTA | TTA | CCA | ATT | TTC | TTT | TGT | CTT | TGG | GTA | TAC | ATT | 845
| Pro | Phe | Leu | Pro | Leu | Leu | Pro | Ile | Phe | Phe | Cys | Leu | Trp | Val | Tyr | Ile |
| | | | | 225 | | | | | 230 | | | | | 235 | |

( 2 ) INFORMATION FOR SEQ ID NO:3:

( i ) SEQUENCE CHARACTERISTICS:
        ( A ) LENGTH: 226 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| | | | | | | | | | | | | | | |
|---|---|---|---|---|---|---|---|---|---|---|---|---|---|---|
| Met | Glu | Asn | Thr | Thr | Ser | Gly | Phe | Leu | Gly | Pro | Leu | Leu | Val | Leu | Gln |
| 1 | | | | 5 | | | | | 10 | | | | | 15 | |
| Ala | Gly | Phe | Phe | Leu | Leu | Thr | Arg | Ile | Leu | Thr | Ile | Pro | Gln | Ser | Leu |
| | | | 20 | | | | | 25 | | | | | 30 | | |
| Asp | Ser | Trp | Trp | Thr | Ser | Leu | Asn | Phe | Leu | Gly | Gly | Ala | Pro | Thr | Cys |
| | | | 35 | | | | 40 | | | | | 45 | | | |
| Pro | Gly | Gln | Asn | Ser | Gln | Ser | Pro | Thr | Ser | Asn | His | Ser | Pro | Thr | Ser |
| | 50 | | | | | 55 | | | | | 60 | | | | |
| Cys | Pro | Pro | Ile | Cys | Pro | Gly | Tyr | Arg | Trp | Met | Cys | Leu | Arg | Arg | Phe |
| 65 | | | | | 70 | | | | | 75 | | | | | 80 |
| Ile | Ile | Phe | Leu | Phe | Ile | Leu | Leu | Leu | Cys | Leu | Ile | Phe | Leu | Leu | Val |
| | | | | 85 | | | | | 90 | | | | | 95 | |
| Leu | Leu | Asp | Tyr | Gln | Gly | Met | Leu | Pro | Val | Cys | Pro | Leu | Leu | Pro | Gly |
| | | | | 100 | | | | | 105 | | | | | 110 | |
| Thr | Ser | Thr | Thr | Ser | Thr | Gly | Pro | Cys | Lys | Thr | Cys | Thr | Ile | Pro | Ala |
| | | | 115 | | | | | 120 | | | | | 125 | | |
| Gln | Gly | Thr | Ser | Met | Phe | Pro | Ser | Cys | Cys | Cys | Thr | Lys | Pro | Ser | Asp |
| | 130 | | | | | 135 | | | | | 140 | | | | |
| Gly | Asn | Cys | Thr | Cys | Ile | Pro | Ile | Pro | Ser | Ser | Trp | Ala | Phe | Ala | Arg |

```
      145                    150                     155                     160
    Phe  Leu  Trp  Glu  Trp  Ala  Ser  Val  Arg  Phe  Ser  Trp  Leu  Ser  Leu  Leu
                        165                     170                     175

Val  Pro  Phe  Val  Gln  Trp  Phe  Val  Gly  Leu  Ser  Pro  Thr  Val  Trp  Leu
                   180                     185                     190

Ser  Val  Ile  Trp  Met  Met  Trp  Tyr  Trp  Gly  Pro  Ser  Leu  Tyr  Asn  Ile
              195                     200                     205

Leu  Ser  Pro  Phe  Leu  Pro  Leu  Leu  Pro  Ile  Phe  Phe  Cys  Leu  Trp  Val
         210                     215                     220

Tyr  Ile
    225
```

( 2 ) INFORMATION FOR SEQ ID NO:4:

( i ) SEQUENCE CHARACTERISTICS:
        ( A ) LENGTH: 817 base pairs
        ( B ) TYPE: nucleic acid
        ( C ) STRANDEDNESS: single
        ( D ) TOPOLOGY: linear ( i i ) MOLECULE TYPE: cDNA from genomic RNA ( x i ) SEQUENCE DESCRIPTION: SEQ ID NO:4:

```
ATACCCATTT GGGATAAGGG TAAACATCTT TGAATTGTCG AAATGAAACG TATATAAGCG        60

CTGATGTTTT GCTAAGTCGA GGTTAGTATG GCTTCATCTC TCATGAGAAT AAGAACGG         118

ACT GGG GAC CCT GCA CCG AAC ATG GAG AAC ACA ACA TCA GGA TTC CTA         166
                                Met Glu Asn Thr Thr Ser Gly Phe Leu
                                 1                       5

GGA CCC CTG CTC GTG TTA CAG GCG GGG TTT TTC TTG TTG ACA AGA ATC         214
Gly Pro Leu Leu Val Leu Gln Ala Gly Phe Phe Leu Leu Thr Arg Ile
 10                  15                      20                  25

CTC ACA ATA CCA CAG AGT CTA GAC TCG TGG TGG ACT TCT CTC AAT TTT         262
Leu Thr Ile Pro Gln Ser Leu Asp Ser Trp Trp Thr Ser Leu Asn Phe
              30                      35                      40

CTA GGG GGA GCA CCC ACG TGT CCT GGC CAA AAT TCG CAG TCC CCA ACC         310
Leu Gly Gly Ala Pro Thr Cys Pro Gly Gln Asn Ser Gln Ser Pro Thr
                 45                      50                      55

TCC AAT CAC TCA CCA ACC TCT TGT CCT CCA ATT TGT CCT GGC TAT CGC         358
Ser Asn His Ser Pro Thr Ser Cys Pro Pro Ile Cys Pro Gly Tyr Arg
             60                      65                      70

TGG ATG TGT CTG CGG CGT TTT ATC ATA TTC CTC TTC ATC CTG CTG CTA         406
Trp Met Cys Leu Arg Arg Phe Ile Ile Phe Leu Phe Ile Leu Leu Leu
         75                      80                      85

TGC CTC ATC TTC TTG TTG GTT CTT CTG GAC TAC CAA GGT ATG TTG CCC         454
Cys Leu Ile Phe Leu Leu Val Leu Leu Asp Tyr Gln Gly Met Leu Pro
 90                  95                     100                     105

GTT TGT CCT CTA CTT CCA GGA ACA TCA ACT ACC AGC ACG GGA CCA TGC         502
Val Cys Pro Leu Leu Pro Gly Thr Ser Thr Thr Ser Thr Gly Pro Cys
              110                     115                     120

AAG ACC TGC ACG ATT CCT GCT CAA GGA ACC TCT ATG TTT CCC TCT TGT         550
Lys Thr Cys Thr Ile Pro Ala Gln Gly Thr Ser Met Phe Pro Ser Cys
          125                     130                     135

TGC TGT ACA AAA CCT CGG ACG GAA ACT GCA CTG TAT TCC CAT CCA             598
Cys Cys Thr Lys Pro Ser Asp Gly Asn Cys Thr Cys Ile Pro Ile Pro
      140                     145                     150

TCA TCC TGG GCT TTC GCA AGA TTC CTA TGG GAG TGG GCC TCA GTC CGT         646
Ser Ser Trp Ala Phe Ala Arg Phe Leu Trp Glu Trp Ala Ser Val Arg
  155                     160                     165

TTC TCC TGG CTC AGT TTA CTA GTG CCA TTT GTT CAG TGG TTC GTA GGG         694
Phe Ser Trp Leu Ser Leu Leu Val Pro Phe Val Gln Trp Phe Val Gly
```

| | | | | | | | | | | | | | | | | |
|---|---|---|---|---|---|---|---|---|---|---|---|---|---|---|---|---|
| 170 | | | | | 175 | | | | | 180 | | | | | 185 | |
| CTT | TCC | CCC | ACT | GTT | TGG | CTT | TCA | GTT | ATA | TGG | ATG | ATG | TGG | TAT | TGG | 742 |
| Leu | Ser | Pro | Thr | Val | Trp | Leu | Ser | Val | Ile | Trp | Met | Met | Trp | Tyr | Trp | |
| | | | | 190 | | | | | 195 | | | | | 200 | | |
| GGG | CCA | AGT | CTG | TAC | AAC | ATC | TTG | AGT | CCC | TTT | TTA | CCG | CTA | TTA | CCA | 790 |
| Gly | Pro | Ser | Leu | Tyr | Asn | Ile | Leu | Ser | Pro | Phe | Leu | Pro | Leu | Leu | Pro | |
| | | | 205 | | | | | 210 | | | | | 215 | | | |
| ATT | TTC | TTT | TGT | CTT | TGG | GTA | TAC | ATT | | | | | | | | 817 |
| Ile | Phe | Phe | Cys | Leu | Trp | Val | Tyr | Ile | | | | | | | | |
| | | 220 | | | | | 225 | | | | | | | | | |